US006785193B2

(12) United States Patent
Forbath

(10) Patent No.: US 6,785,193 B2
(45) Date of Patent: Aug. 31, 2004

(54) MEDICAL TIMING SYSTEM FOR USE BEFORE AND DURING CHILDBIRTH LABOR

(76) Inventor: Frank P. Forbath, 2880 Club House Rd., Costa Mesa, CA (US) 92626-4760

(*) Notice: Subject to any disclaimer, the term of this patent is extended or adjusted under 35 U.S.C. 154(b) by 0 days.

(21) Appl. No.: 09/886,415

(22) Filed: Jun. 20, 2001

(65) Prior Publication Data

US 2002/0015361 A1 Feb. 7, 2002

Related U.S. Application Data

(60) Provisional application No. 60/212,872, filed on Jun. 20, 2000.

(51) Int. Cl.[7] ......................... G04F 10/00; G04B 19/00; A61B 5/00

(52) U.S. Cl. ......................... 368/108; 368/10; 368/108; 368/111; 368/223; 600/304

(58) Field of Search ........................... 368/10, 107–113, 368/223, 251, 72–73; 600/304, 588, 591; 700/15; 702/178

(56) References Cited

U.S. PATENT DOCUMENTS 4,403,777 A * 9/1983 Del Principe et al. .......... 463/1
4,493,043 A 1/1985 Forbath
4,711,585 A * 12/1987 Fresquez .................... 368/109
5,042,503 A * 8/1991 Torok ......................... 600/558
5,377,170 A 12/1994 Blaylock et al.
5,876,335 A * 3/1999 Handy ........................ 600/304
5,876,357 A * 3/1999 Tomer ........................ 600/591
6,122,559 A * 9/2000 Bohn .......................... 700/91

* cited by examiner

*Primary Examiner*—Randy W. Gibson
*Assistant Examiner*—Michael L. Lindinger

(57) ABSTRACT

A handheld childbirth labor timing apparatus includes a timing device with a visible display, a calculating device, a memory device and a selection device. In various embodiments the apparatus is programmed to execute methods for the simple timing of the durations of and intervals between actual childbirth contractions, for practicing selected sequences of such contractions in preparing for childbirth, and also for storing a set of expected sequences that, when matched, with an actual childbirth labor sequence will present an alerting signal to the user so as to timely summon medical help.

6 Claims, 3 Drawing Sheets

MEDICAL TIMING SYSTEM FOR USE BEFORE AND DURING CHILDBIRTH LABOR

The present invention claims the priority date of a prior filed provisional patent application having Serial No. 60/212,872 and an official filing date of Jun. 20, 2000 and which discloses substantially the same invention as described herein.

BACKGROUND OF THE INVENTION

1. Field of the Invention

This invention relates generally to hand-held timers and calculators and more particularly to such a timer and calculator enabled for providing benefit during human pregnancy.

2. Description of Related Art

The following art defines the present state of this field:

Blaylock et al., U.S. Pat. No. 5,377,170 describes a timer which measures the duration of a first of two consecutive contractions and also measures the elapsed time period between the beginning of said first contraction and the beginning of a second of two consecutive contractions and which displays successive pairs of first and second contractions and which also compares the most recent time measurement values to a user programmed target time and further alerts the user when a measured time is less than said programmed target time.

Handy et al., U.S. Pat. No. 5,876,335 describes a multipurpose pregnancy and labor timing device for use by expectant parents during the gestation, labor, and birth of their child. The timing device includes an output device for conveying a plurality of datum to a human observer. The datum conveyed may represent a current time, day and date, an expected date of birth of the child, an estimated elapsed time period since the conception date of the child, an estimated time period until the birth of the child, the count of contractions experienced by a woman undergoing the process of labor, the time interval between contractions, the duration of a contraction, and the actual time and date of the birth of the child. The timing device also includes a nonvolatile memory for storing at least some of the plurality of datum, a data selection device for selecting at least some of the plurality of datum for conveyance by the output device, and a data initialization device for initializing the first datum and the second datum. The timing device further includes a processor control device for performing a first sequence of operations to store at least some of the plurality of datum into the nonvolatile memory, for performing a second sequence of operations to retrieve at least some of the plurality of datum from the nonvolatile memory so that at least some of the plurality of datum is conveyed by the output device, and for calculating at least some of the plurality of datum.

Of particular and specific importance is U.S. Pat. No. 4,493,043 to Forbath. This reference teaches a medical timing system having a programmed, computer controlled, display and audible buzzer, with inputs from a timing switch and readout button which are connected together so that pregnancy labor pains may be timed, contraction patterns may be rehearsed by an expectant mother, and fetus movements may be counted. The medical timing system is preferably hand-held and compact so that the timing switch and readout button may be easily actuated and so that accurate and reliable timing measurements may be made and recorded through use of the system.

The prior art teaches the use of timing devices for childbirth labor but does not teach an apparatus and method that is more easily accommodated during the stressful time of actual labor and childbirth, which allows a convenient means for practicing in harmony with modern childbirth practice techniques and which may be set as an alert device to indicate when medical help should be summoned. Specifically, Handy does not teach the use of a memory device used for duration and interval time storage. Blaylock teaches an alert only for less than a preselected interval. The present invention fulfills these needs and provides further related advantages as described in the following summary.

SUMMARY OF THE INVENTION

The present invention teaches certain benefits in construction and use which give rise to the objectives described below.

The present invention teaches substantial advances over a precursor patented invention, the '043 patent described above, and the prior art. Through our experience with pregnant women with a precursor device manufactured in accordance with the precursor patent, it has been discovered that improved construction design and operation is necessary to achieve an acceptable operating product for use in the very stress laden situation of childbirth. In such situation, the user cannot remember simple steps and numbers but can read simple instructions or reminder words and phrases and can recall numbers in a device memory. Thus, the improved shape and size and operating characteristics (methods) of the present invention have been discovered through a long and yet effective invention process which results in the present invention apparatus and method of use.

The present invention is a handheld childbirth labor timing, practicing and alerting apparatus which includes a timing circuit with a visible display, a calculating means, a memory device and a user selection means. In various embodiments the apparatus is programmed to execute methods for the simple timing of the durations of and intervals between actual childbirth contractions, for practicing selected sequences of such contractions in preparing for childbirth, and also for storing a set of expected sequences that, when matched, with an actual childbirth labor sequence presents an alerting signal to a user so as to timely summon medical help. This apparatus is designed for a user training for childbearing as well as for having support during childbearing. It also provides a psychological "crutch" which a pregnant woman may rely upon during this period of great emotional and physical stress.

The apparatus records labor contraction durations and intervals between them as a timing sequence. It also may be programmed to provide a warning when the user enters the onset of childbearing, i.e., when one or more actual timing sequences which are entered into the memory of the apparatus during labor matches a prerecorded childbirth timing sequence used for alerting the user that medical help should be summoned. In this mode of operation, typically, medical staff may ask the user to make contact when certain timing sequences occur. Such a prerecorded timing sequence may be, for example, when contraction durations are at least 60 seconds, or when there are 4 or more contractions of 50 seconds duration, or when contraction intervals are 7 minutes apart, etc. Such a request may consist of the conjunction of two or more timing sequence conditions or may be expressed in the alternative. In either case, or even a combination of conjunction and alternative sequences, the subject apparatus is able to match actual with prerecorded sequences and trigger the alert. This ability can be critically important in certain circumstances.

In the present text the term, "medical staff" shall mean a medical doctor, obstetrician, midwife, nurse or other medically trained personnel or person standing-in for same; the term, "user" shall mean the woman preparing for childbirth, her spouse, her birthing coach or other individuals performing similar roles and who actually manipulate and interpret results in the use of the subject invention; the term, "contraction duration" shall mean the amount of time from the start to the end of an individual labor contraction; and the term, "contraction interval" shall mean the amount of time between the start of two successive contractions, although an alternative interpretation may be substituted. Likewise, the term, "icon" shall mean a pictorial representation, "acronym" shall mean a string of letters representing a literal term or an abbreviation, such as LED for light emitting diode, LCD for liquid crystal display, PCB for printed circuit board and ASIC for application-specific integrated circuit.

The invention apparatus includes an LCD display which is programmed to provide a variety of visual information to the user while using relatively little electrical energy. A rubber key pad provides user control of the device through electrically conducting surfaces positioned and enabled for closing circuits on a PCB. An ASIC, or other computational device, is enabled for driving the LCD display, controlling the apparatus operation, providing and recording time, calculating time intervals, recording data, comparing current and prerecorded data, driving an audible signaling device, and providing power on and power off functions. A plastic case incorporates surfaces enabled for retaining batteries and beepers that have electrical surface contacts and surfaces adapted for retaining electrical contacts. This avoids soldering steps in assembly. A backlighted display can be used with the apparatus for viewing in low light conditions. Generally speaking, the present apparatus is constructed using the latest manufacture techniques and parts to accomplish a highly cost effective result.

A primary objective of the present invention is to provide an apparatus and method of use of such apparatus that provides advantages not taught by the prior art.

Another objective is to provide such an invention capable of very low manufacturing cost.

A further objective is to provide such an invention capable of improved manual gripping, manipulation and communicating.

A further objective is to provide such an invention capable of improved method of timing labor sequences.

A further objective is to provide such an invention capable of improved birth labor training methods.

A further objective is to provide such an invention capable of alerting a user to the point in time when medical support should be summoned.

A further objective is to provide such an invention capable of providing the physical and operational elements in such a device necessary for beneficial use under the extreme stress of childbirth.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

Figure 4:
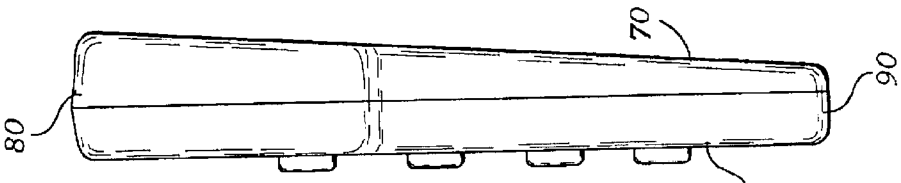
FIG. 4 is a side view thereof.

The above described drawing figures illustrate the invention in several of its preferred embodiments, which is further defined in detail in the following description.

The present invention is a hand held apparatus as shown in FIGS. 1–4 and includes a novel method of use. It is used, advantageously, during the pregnancy period of a user. The apparatus comprises an enclosure case 10, of essentially rectangular shape, providing a lower portion 20 having a width 30 enabled by its size for being enclosed within the palm of one hand, and an upper portion 40 of greater width than the lower portion 20 so as to provide space for functional elements. A pair of opposing shoulders 50, 50' provide transitioning between the lower 20 and upper 40 portions. The case 10 further comprises a front 60 and a back 70 panels, where these panels are set in convergent juxtaposition between a top 80 and bottom 90 surfaces of the case 10 as is clearly shown in FIG. 4. This shape, with its shoulders and convergent panels has been found to be of great advantage to the user during actual childbearing. During this time, the user is under stress and is not able to think clearly. Therefore, a symmetrical case is easily grasped in an inverted, or otherwise wrong, attitude so as to add to the confusion of the moment. The subject invention is not easily grasped wrongly because of the difference in case width between the lower 20 and upper 40 portions, because of the shoulders 50, 50' and because of the convergent front and back panels 60, 70. These three elements of asymmetry provide a tactile control mechanism to achieve a proper positioning of the device by feel alone.

The front panel 60 provides a visible display 100, selection means 110, preferably actuation buttons as shown, and to be further described below, and a sound port 120 concealing an audible device 130. The case 10 also encloses a timing device 140, a calculating means 150 and a memory device 160. The visual display 100 is preferably an LCD display which is programmed to provide a variety of visual information to the user while using relatively little electrical energy due to the fact that such a display draws a small current. A rubber touch pad provides user control of the device through electrically conducting surfaces positioned and enabled by the selection means 110 for closing circuits on a PCB. An ASIC is enabled for driving the LCD display and an audible device 130 and it contains an instruction set for controlling operation of the apparatus and the memory device 160 which preferably combines volatile and non-volatile memory types, well known in the art, for storing input, and output information as well as factory installed practice patterns. The case 10 is preferably of a plastic molded type and incorporates surfaces enabled for retaining the LCD display and its connecting rubber pad which incorporated conduction surfaces that enable connection between the LCD and the PCB, batteries, the audible device 130 and other components that have electrical surface contacts and surfaces adapted for retaining electrical contacts. This avoids soldering steps in assembly and enables the apparatus to be manufactured with low cost. The present inventor's precursor patent, U.S. Pat. No. 4,493,043 teaches certain specific circuit enablements which may be used to reduce the present invention to practice. The document is hereby incorporated into this application by reference. As an example, the circuit of FIG. 2*a* in the precursor patent may be used in the present invention with only slight modifications.

Several preferred embodiments of the present invention use selected user control buttons (selection means 110) to accomplish the useful objects as defined above. A two button system is a basic labor contraction timer. A four button system additionally enables the user to practice labor patterns. An alternative four button system provides the basic timer plus a programmable alert function, and a six button system provides all three functions. These systems will be further described in detail below.

Figure 1:
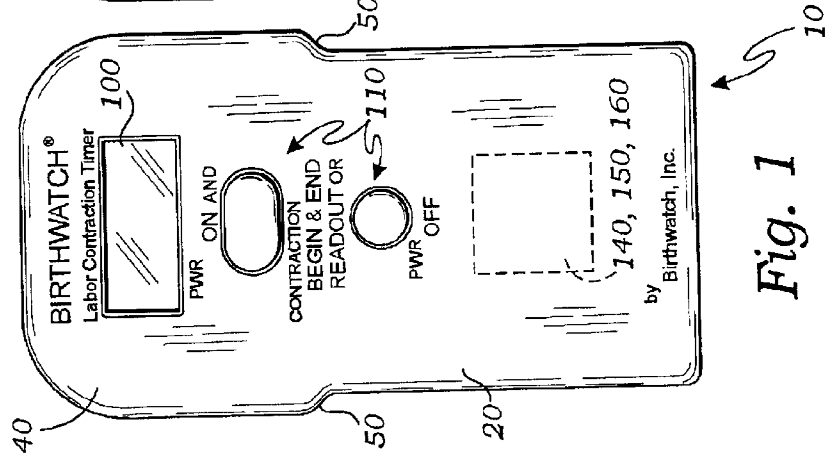
Figure 6:
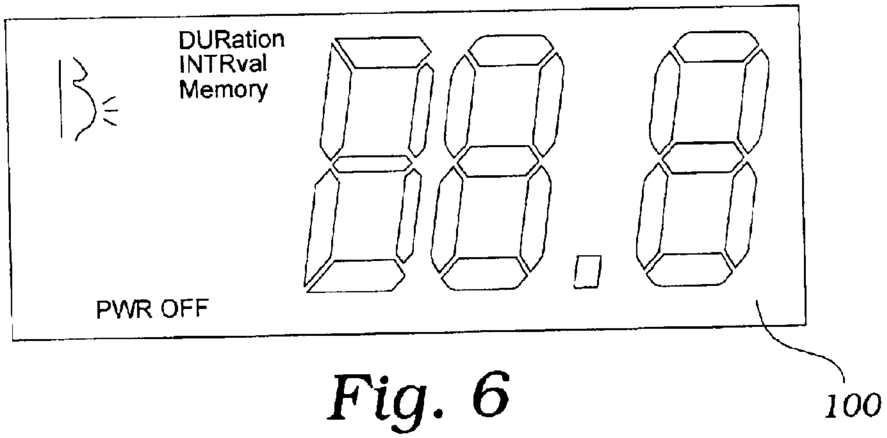
Figure 7:
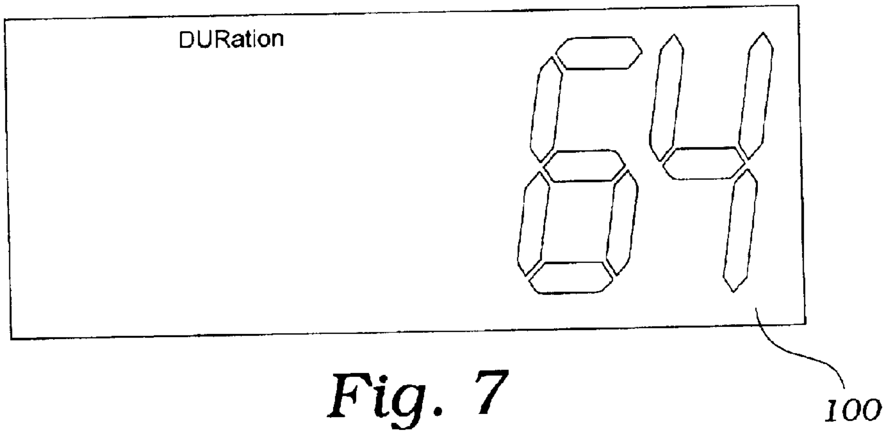

The two button timing apparatus, shown in FIG. 1, provides certain methods of use including a method of timing childbirth labor contractions comprising the steps of: selecting an initiation time, $t_{1(i)}$, for each of a plurality of labor contractions (i), where i=1, 2, 3 . . . at the onset of each, as determined by the user; displaying elapsed contraction time, in seconds, during each of the contractions on the visible display 100, as shown in FIG. 7; selecting a termination time, $t_{2(i)}$, for each of the labor contractions at the diminution thereof, again as determined by the user; calculating a time interval between each adjacent pair of the contractions, where this is programmed to occur automatically using the calculating means 150; calculating a contraction time duration for each of the contractions; storing each of the time intervals and time durations in the memory device 160; and displaying the time durations and intervals in sequence upon selection by the user including a visual indication on the display distinguishing between a time duration display and a time interval display, preferably using the word "Duration" for a duration display, and the word, "Interval" an interval time display as shown in FIG. 6. The time interval between any contractions A and B is found by subtracting $t_1$ for contraction A, from $t_1$ for contraction B, the immediately preceding contraction. Alternate definitions of contraction interval may be used. The contraction duration is found by subtracting $t_1$ from $t_2$ for the ith contraction, i.e., $t_2(i)$-$t_1(i)$, where "i" represents any selected contraction.

In this two button system, the front panel provides two buttons which, together, comprise the selection means 110 as shown in FIG. 1, as follows:

"Power On/Contraction Begin & End" provides the functions of, first, setting device power to the active state by a momentary actuation, and second, signaling the start of a contraction by a second momentary actuation. Alternately both of the foregoing functions can be attained simultaneously by a single extended actuation. A subsequent momentary actuation signals the end of the contraction. This start of, and end of, contraction signaling may be repeated sequentially with this control.

"Read Out/Power Off" provides the functions of, first, generating a display of the duration of the last contraction by a momentary actuation, then generating a display of the interval between the next to last contraction and the last contraction by a further momentary actuation. Further displays of prior contraction durations and intervals are displayed by further momentary actuations until all of the stored data are displayed and then an indication for memory end is show prior to the cycle repeating through further actuations. An extended actuation turns device power to the inactive or power off state.

Additionally, in this embodiment, as shown in FIG. 6, the visible display 100 provides the words, "Duration," "Interval" and "Memory" with are enabled at appropriate times in the process and in addition other text in the seven segment readouts are displayed, e.g., "du," "In," and "End." When $t_1$ and, later, $t_2$ are entered "Duration" appears on the display 100.

When an interval is retrieved, the word "Interval" appears on the display 100. In this manner, the user is able to understand what each retrieved number represents.

Figure 2:
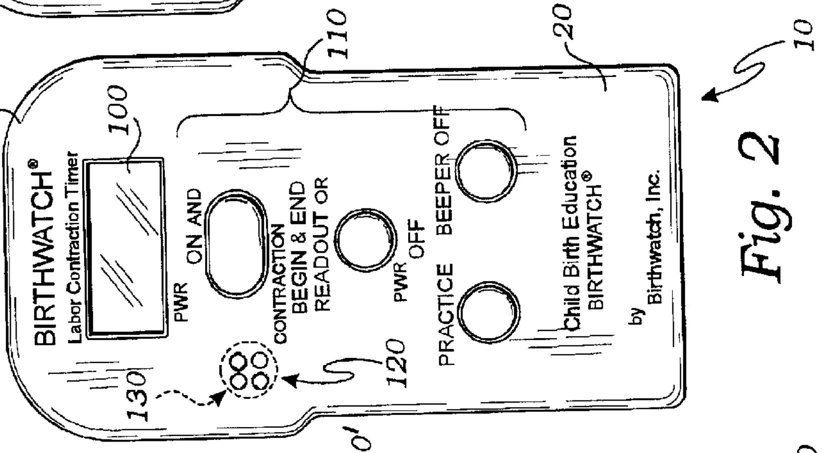

In a further, four button embodiment, two additional control panel buttons are provided as follows and as shown in FIG. 2:

"Practice" provides the function of setting the device into a practice mode in the first of four states: Early Labor, Active Labor, Transition Labor, and Pushing Labor, wherein each of these states is achieved, in turn, through subsequent momentary actuations and are repeated in the same order through further momentary actuations.

"Beeper Off" toggles enablement of the audible device 130 which is preferably set to the enabled state upon startup.

Figure 5:
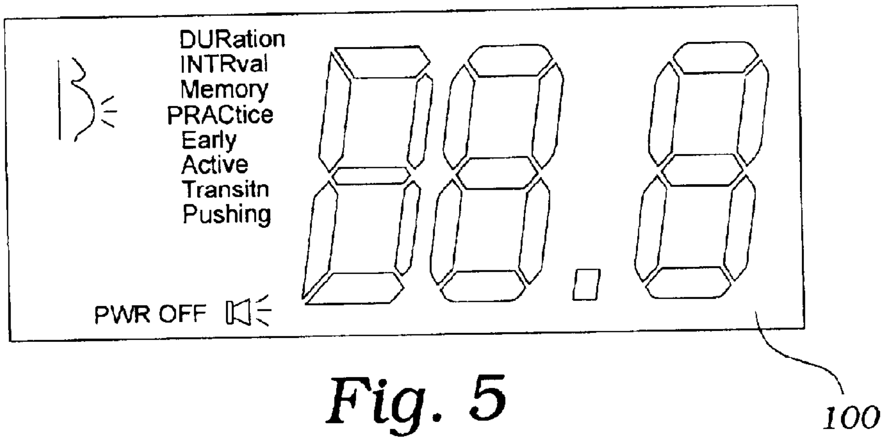
FIGS. 5–9 are front views of a visual LCD display device illustrating various displayed configurations according to the invention.

In this, second embodiment, as shown in FIG. 2, the present invention method comprises further steps, for instance, such that the apparatus may be used as a tool for practicing, or training, using modern methods of childbirth labor. Such methods include storing a plurality of childbirth labor practice instruction sets in the memory device 60. The memory device 60 provides a non-volatile portion so that these instruction sets are permanently stored for future use even when power is turned off and when the battery is removed from the apparatus. Preferably, the instruction sets include separate: early labor, active labor, transition labor, and pushing labor instruction sets. These phases of childbirth labor are well known in the art and are distinguished apart by duration and frequency of contractions, as well as the many physical effects involved. The instruction sets are designed to simulate such childbirth labor sequences and patterns. After selecting one of the practice sets through the selecting means 110, the calculating means 150 immediately calculates a plurality of contraction durations and contraction intervals using a random number generator incorporated as part of the calculating means. A running time of each of a plurality of contractions is then displayed, in sequence, on the visible display 100, along with audible indicators at start, periodically during and at the end, enabling the user to perform the desired breathing and exercising actions. FIG. 5 shows the visual display device 100 relevant to this embodiment.

Figure 3:
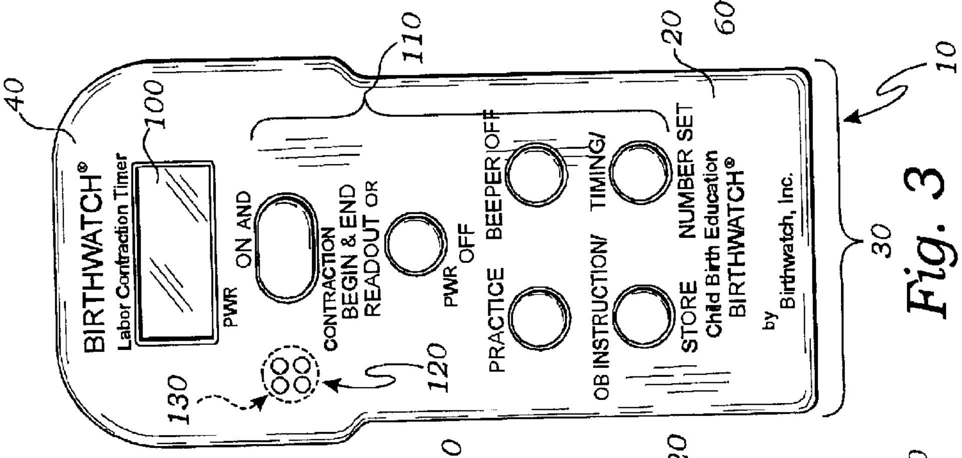
FIGS. 1–3 are front elevation views of a housing of the present invention according to several embodiments thereof.

In a further embodiment of the present invention, a six button control panel provides an additional set of two buttons in the selection means 110, as shown in FIG. 3 and described as follows:

"OB Instruction/Store" provides the function of setting the device into an instruction mode in one of the states defined as: Interval, Duration, Number, Or, and And, and advancing to each subsequent state thereafter through momentary actuations and further stores the prior changes as defined in the next paragraph.

"Timing/Number Set" operates in conjunction with the "OB Instruction Store" button for selecting a corresponding interval time, duration time, number (of contractions having greater than the selected duration time and/or number of intervals of less than the selected interval time), the Boolean "or" function, and the Boolean "and" function.

In this embodiment, the method comprises further steps, such that the apparatus may be used as a tool for providing an alert to the user when her state of labor has progressed to a point where she would be advised to seek medical help.

Figure 8:
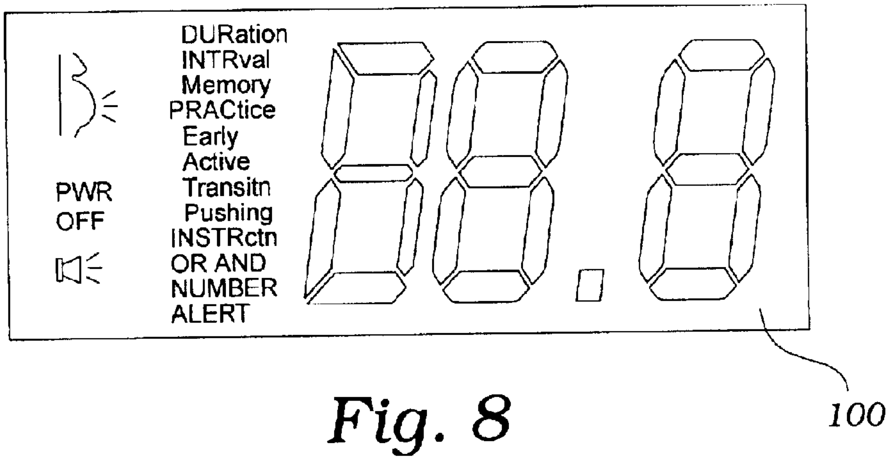

Prior to actual labor, these further steps include : selecting from a plurality of values of labor contraction durations, labor contraction intervals and labor contraction quantities, one or more alert parameters defined by numbers from a predetermined set of numbers, representing seconds where the displayed values represent labor contraction durations and minutes where the displayed values represent labor contraction intervals, and number of labor contractions having the desired timing values, each labeled for identification on the visual display; storing the alert parameter(s) in the memory device 160; selecting by the user during childbirth labor an initiation time $t_1$ and a termination time $t_2$ for each of a plurality of actual sequential labor contractions; calculating a time interval between each adjacent pair of the contractions, as described above; calculating a contraction time duration, as described above, for each of the contractions; storing each of the contraction duration times and each of the interval times in the memory device 160; and enabling an alert action, such as activation of the audible device 130, and/or a blinking icon or text on the visual display, as shown in FIG. 5, when a match occurs between the selected alert parameter(s) and an actual labor sequence. Of course, the calculations and matching are completed automatically, as part of the programmed instruction set, by the calculating means 150 as would be within the ability of one of skill in the art. FIG. 8 shows the visual display device 100 relevant to this embodiment, wherein all the digit segments, text and icons are shown briefly upon Power On, and the appropriate portions are displayed as needed per above discussion.

Figure 9:
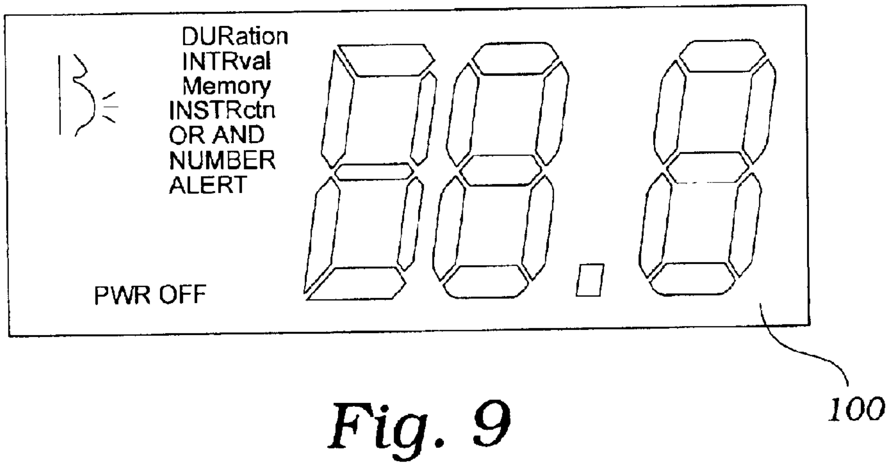

The present invention may be configured for only contraction timing and alert functions but without the practice function in a still alternate four button system. FIG. 9 shows the visual display device 100 relevant to this embodiment. Other configurations of the present apparatus and method are possible within the scope of the present invention.

While the invention has been described with reference to several preferred embodiments, it is to be clearly understood by those skilled in the art that the invention is not limited thereto. Rather, the scope of the invention is to be interpreted only in conjunction with the appended claims.

What is claimed is:

1. A labor contraction duration and interval timing method comprising the steps of:

providing, a hand held apparatus having a visible display, an audible device, a touch pad, a timing device, a calculating means, a mode selector and a memory device; wherein in practice mode:

storing in the memory device, a plurality of random contraction durations, random contraction intervals and contraction quantities, as at least one practice set;

indicating on at least one of the visible display and the audible device, an initiation time and a termination time for each of a plurality of practice labor contractions, at the onset and diminution thereof respectively;

displaying the practice durations and intervals in sequence on the visible display;

and, in labor timing mode:

selecting an initiation time an a termination time for each of a plurality of actual labor contractions, at the onset and diminution thereof respectively;

calculating an actual contraction duration for each of the plurality of actual labor contractions, and an actual contraction interval between each adjacent pair of the actual labor contractions;

displaying the actual durations and actual intervals in sequence on the visible display;

and, in alert mode:

selecting an alert set comprising alert minimum durations, alert maximum intervals, alert quantities of said durations and intervals, and Boolean operators;

selecting an initiation time and a termination time for each of a plurality of actual labor contractions, at the onset and diminution thereof respectively;

calculating an actual contraction duration for each of the plurality of actual labor contractions, and an actual contraction interval between each adjacent pair of the actual labor contractions and counting the contraction duration and interval quantities;

displaying the actual durations and actual intervals in sequence on the visible display;

enabling at least one of the visible display and the audible device when the actual durations, actual intervals and actual quantities match the alert set.

2. The method of claim 1 further comprising the step of providing a button of the touch pad enabling the functions of, first, setting device power to the active state by a momentary actuation, and second, signaling the start of a contraction by a second momentary actuation, and alternately completing the power setting and starting simultaneously by a single extended actuation, and signaling contraction end by a further momentary actuation thereof.

3. The method of claim 1 further comprising the step of providing a button of the touch pad enabling the functions of, first, generating a display of the duration of the last contraction by a momentary actuation, then generating a display of the interval between the next to last contraction and the last contraction by a further momentary actuation and enabling further displays of prior contraction durations and intervals by further momentary actuations until all of the stored data are displayed.

4. The method of claim 1 further comprising the step of providing a button of the touch pad enabling the function of setting the device into a practice mode in the first of four states: Early Labor, Active Labor, Transition Labor, and Pushing Labor, wherein each said state is achieved, in turn, through subsequent momentary actuations and repeated in the same order through further momentary actuations.

5. The method of claim 1 further comprising the step of providing a button of the touch pad enabling the function of setting an instruction mode in one of the states defined as: Interval, Duration, Number, Or, and And, and advancing to each subsequent state thereafter through momentary actuation.

6. The method of claim 1 further comprising the step of providing a button of the touch pad enabling selecting a corresponding interval time, duration time, number of contractions and Boolean operators.

* * * * *